(12) United States Patent
Frost

(10) Patent No.: US 7,290,924 B2
(45) Date of Patent: Nov. 6, 2007

(54) NON-BOIL BOILING POINT INDICATOR

(75) Inventor: Derek E. Frost, Saint Andrews (GB)

(73) Assignee: Liquid Levers Innovations Ltd, Fife (GB)

( * ) Notice: Subject to any disclaimer, the term of this patent is extended or adjusted under 35 U.S.C. 154(b) by 189 days.

(21) Appl. No.: 10/871,607

(22) Filed: Jun. 21, 2004

(65) Prior Publication Data
US 2005/0013340 A1    Jan. 20, 2005

Related U.S. Application Data
(63) Continuation of application No. PCT/GB03/01668, filed on Apr. 17, 2003.

(30) Foreign Application Priority Data
Apr. 17, 2002 (GB) ................ 0208763.3

(51) Int. Cl.
*G01N 25/00* (2006.01)
(52) U.S. Cl. .................. 374/27; 374/16
(58) Field of Classification Search .......... 374/27
See application file for complete search history.

(56) References Cited
U.S. PATENT DOCUMENTS

| | | | |
|---|---|---|---|
| 4,484,822 A | 11/1984 | Hancock | |
| 4,484,823 A | 11/1984 | Peuker | |
| 4,869,596 A | 9/1989 | Klein et al. | |
| 4,958,937 A * | 9/1990 | Lohberg et al. | 374/16 |
| 5,330,268 A | 7/1994 | Klein et al. | |
| 5,380,091 A | 1/1995 | Buchanan | |
| 5,563,337 A | 10/1996 | Fitch et al. | |
| 6,433,693 B1 | 8/2002 | Matthew, Jr. | |

FOREIGN PATENT DOCUMENTS

GB    2 139 763    11/1984

(Continued)

OTHER PUBLICATIONS

IBM Technical Disclosure Bulletin—Floating Type Boiling Point Sensor, Order/Fcode/Docket: 71C 00418/18-014, 49-400./ p08700016, Jan. 1971, p. 1 of 1 (1 page).

*Primary Examiner*—Diego Gutierrez
*Assistant Examiner*—Mirellys Jagan
(74) *Attorney, Agent, or Firm*—Shlesinger, Arkwright & Garvey LLP

(57) ABSTRACT

Non-boil boiling point indicator includes a probe housing having inner and outer chambers and a heater located within the inner chamber at a free end of the probe housing. The probe housing has a free end provided with non-restrictive apertures. Similar non-restrictive apertures are located between the inner and outer chambers and from the outer chamber to an outer environment surrounding the probe housing. The temperature of the test fluid is monitored by a temperature monitoring device. As the test fluid is rapidly heated, its temperature quickly rises then flattens out before boiling point. This change is used to extrapolate to the boiling point. Localized steam or vapor bubbles are created next to the heater, which causes the test fluid above the heater to be propelled upwards and overflow through the unrestricted apertures at the top of the inner chamber into the outer chamber.

15 Claims, 3 Drawing Sheets

FOREIGN PATENT DOCUMENTS

| | | |
|---|---|---|
| GB | 2 200 997 | 8/1988 |
| GB | 2 287 321 | 9/1995 |
| WO | 90/12311 | 10/1990 |
| WO | 95/24646 | 9/1995 |
| WO | 95/30899 | 11/1995 |
| WO | 03/089914 | 10/2003 |

* cited by examiner

NON-BOIL BOILING POINT INDICATOR

CROSS REFERENCE TO RELATED APPLICATIONS

This application is a continuation application of the U.S. application Ser. No. PCT/GB03/01668, filed Apr. 17, 2003, which claims the priority of Great Britain application no. 02 08 763.3, filed Apr. 17, 2002.

FIELD OF INVENTION

This invention relates to a non-boil boiling point indicator device used to determine the boiling point of a fluid.

BACKGROUND TO THE INVENTION

Hand held boiling point test devices are well known and they consist usually of a 'probe' housing containing heating elements and temperature monitoring devices. These known devices heat the test fluid within the probe housing using the heating elements and monitor the temperature rise within the fluid, usually taking the maximum temperature attained as the boiling point. Some of these testers use substantially restricted openings (approx. 1 mm) for fluid flow to and from the probe housings to create oscillations at boiling point so as to discern the boiling point. Other such devices use an air lock within the probe housing to isolate the test fluid from the reservoir during the time the test fluid is heated to its boiling point.

The main commercial use of these test devices is the testing of the boiling point of the Hygroscopic Brake Fluid used, for example, in motor vehicle brake systems. The known boiling point test devices are, however, not quick enough, not suitable for receiving replaceable or rechargeable batteries, or capable of on-vehicle testing of fluids in shallow brake fluid reservoirs.

OBJECTS AND SUMMARY OF THE INVENTION

It is an object of the present invention to provide a non-boil boiling point indicator device in which at least some of the above mentioned disadvantages are substantially overcome, or at least provide an alternative choice for users.

According to the invention there is provided a non-boil boiling point indicator device, including a probe and a control and electronic display means connected with the probe, the probe comprising a housing having inner and outer chambers therein for receiving fluid to be tested, a plurality of non-restrictive apertures located between the inner and outer chambers and between the chambers and an external environment surrounding the probe housing, heater means for heating fluid in the inner chamber and a temperature sensing device located in the inner chamber for sensing the temperature of a fluid being heated in the inner chamber, wherein, in use, a change in the rate of temperature rise is detected by the control and electronic display means to equate to a preselected temperature reading, and wherein steam or vapor bubbles created adjacent the heater means propel non-boiling test fluid above the heater means relative to the direction of insertion of the probe in a fluid to be tested to overflow through the non-restrictive apertures between the inner and outer chambers, which are at the top of the inner heating chamber into the outer chamber.

In one embodiment in accordance with the present invention the non-restrictive apertures are of a size allowing unrestricted vapor bubble flow therethrough.

Preferably, the non-restrictive apertures between the inner and outer chambers are located at a top end of both inner and outer chambers.

Preferably, the non-restrictive apertures interconnecting the outer chamber and external environment are located at a bottom end of the outer chamber. The inner chamber is preferably closed at its innermost end and extends towards the free end of the probe housing, a portion of a wall of the inner chamber defining a gap between it and the probe housing to define in part the outer chamber.

Conveniently, another portion of the wall of the inner chamber engages the inner surface of the probe housing to close the outer chamber. The another portion of the wall of the inner chamber may be thicker in a diametrical direction than the one portion of the inner chamber, to restrict the volume of the inner chamber and thereby minimize the amount of fluid heated by the heater.

Preferably, the inner chamber and probe are closed at the free end thereof by a closure member having a plurality of non-restrictive apertures therethrough to allow free flow of fluid into and out of the inner chamber. The heater may comprise a heater element in the form of a wound coil.

In another embodiment in accordance with the present invention a non-boil boiling point indicator device, includes a probe and a control and electronic display means connected with the probe, the probe comprising a housing extending from the control and electronic display means and having inner and outer chambers therein for receiving fluid to be tested, a plurality of non-restrictive apertures located between the inner and outer chambers and from the outer chamber through the probe housing, a heater for heating fluid in the inner chamber in use, and a temperature sensing device located in part in the heater in the inner chamber for monitoring the temperature of the fluid being heated in the inner chamber, the inner and outer chambers being defined by a tubular sheath of reduced diameter relative to the internal diameter of the probe housing thereby to produce the inner housing within the sheath and the outer chamber between the sheath and internal surface of the probe housing, a shroud extending from the sheath to engage the internal surface of the probe housing to close the outer chamber and to restrict the volume of the inner chamber in the region of the heater, and a closure member extending across a free end of the probe housing remote from the control and electronics display means, the closure member comprising at least one non-restrictive aperture extending therethrough, wherein, in use, a change in the rate of temperature rise is detected by the control and electronic display means to equate to a preselected temperature reading, and wherein steam or vapor bubbles created adjacent the heater can propel non-boiling test fluid above the heater relative to the direction of insertion of the probe in a fluid to be tested to overflow through the non-restrictive apertures between the inner and outer chambers, which are at the top of the inner chamber, into the outer chamber and out of the housing.

The invention also includes a non-boil boiling point indicator device for determining the boiling point of fluids, the device including a probe and a control and display device connected with the probe, the probe including:

a housing having first and second chambers defined therein and being provided with respective non-restrictive apertures for providing fluid communication between the first chamber and the second chamber and the second chamber and an exterior of the housing;

a heating device for heating a fluid to be tested in the first chamber; and a temperature sensor for sensing the temperature of the fluid in the first chamber;

the control and display device is arranged to determine a boiling point temperature for the fluid in the first chamber using a sensed temperature that is lower than the boiling point temperature, which sensed temperature is sensed at a time at which the control and display device determines a decrease in a rate of temperature rise in the fluid based on temperature sensed by the temperature sensor; and the non-restrictive apertures are arranged such that, in use, bubbles formed in the fluid in the first chamber can drive non-boiling the fluid from the first chamber into the second chamber and to the exterior of the housing.

The invention also includes a non-boil boiling point indicator device for determining the boiling point of fluids, the device comprising a housing to be inserted in a fluid to be tested and a control and display device, the housing containing a first chamber and a second chamber, a heating device for heating fluid to be tested in the first chamber and a temperature sensing device for sensing temperature of the fluid in the first chamber, a plurality of non-restrictive apertures being provided in the housing and arranged such that, in use, bubbles generated by heating the fluid in the first chamber can drive non-boiling fluid from the first chamber out of the housing via the second chamber; and the control and display device receiving signals from the temperature sensing device and being adapted to determine a temperature indicative of a boiling temperature of the fluid in the first chamber from at least one sensed temperature lower than the boiling point temperature, the at least one sensed temperature being selected for the determination when signals from the temperature sensing device indicate a decrease in rate of temperature rise indicative of an approach to boiling point of the fluid in the first chamber but substantially before the boiling point is reached.

The invention also includes a method of determining the boiling point of a fluid without boiling the fluid, the method including:

inserting a probe into a container of a fluid whose boiling point is to be determined, the probe having an inner chamber and an outer chamber and being provided with non-restrictive apertures communicating between the inner and outer chambers and between the outer chamber and the exterior environment, insertion of the probe into the fluid causing fluid to be received in the inner chamber;

heating the fluid in the inner chamber, bubbles created in the fluid by the heating thereof being able to freely propel fluid from the inner chamber to the outer chamber via the non-restrictive apertures communicating between the inner and outer chambers to overflow through the non-restrictive apertures communicating between the outer chamber and the exterior environment;

sensing the temperature of the fluid in the inner chamber;

monitoring the sensed temperature to detect a predetermined rate of temperature rise; and determining the boiling point temperature of the fluid using at least one temperature sensed when the predetermined temperature rise is detected, the at least one temperature being substantially below the boiling point temperature.

BRIEF DESCRIPTION OF THE DRAWINGS

Embodiments of the invention will now be described by way of example with referenced to the accompanying drawings in which.

DETAILED DESCRIPTION OF THE INVENTION

Figure 1:
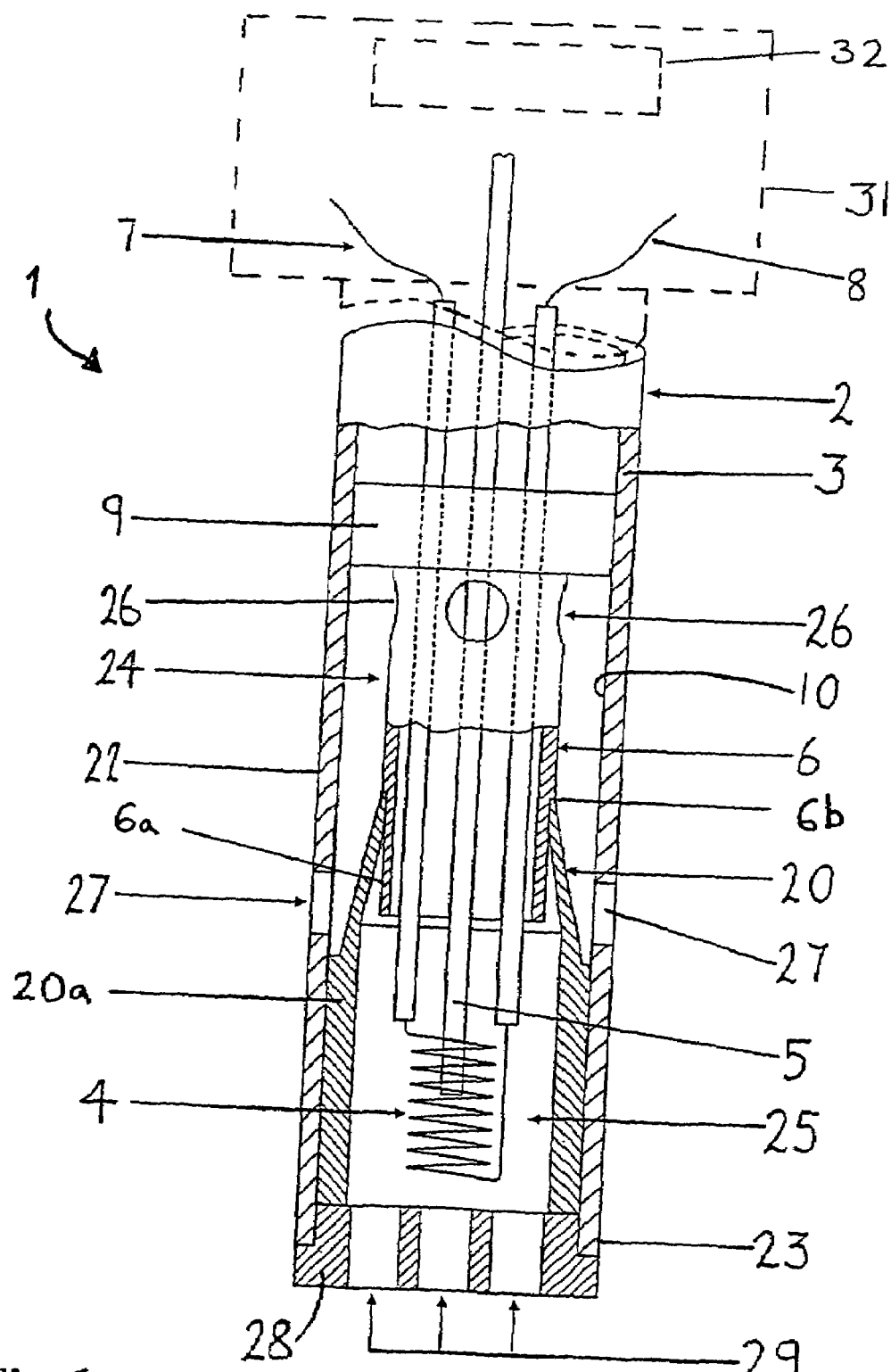
FIG. 1 is a partial cross-sectional view of an embodiment of a non-boiling point test device in accordance with the invention.

Throughout this specification and in the drawings like parts will be referred to by the same reference numerals.

Figure 2:
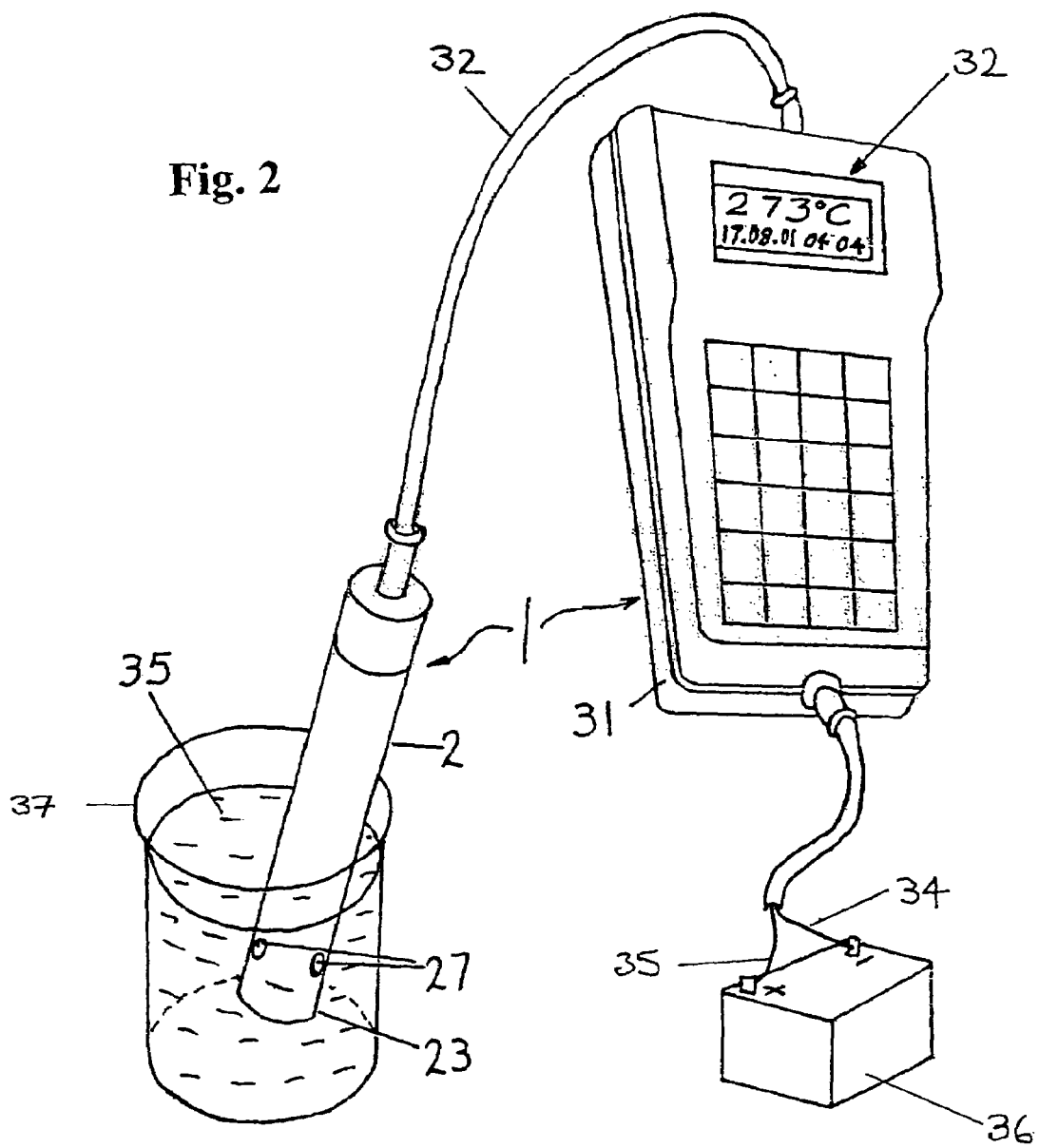
FIG. 2 is a perspective view of another embodiment of a non-boiling point test device in accordance with the invention and illustrating a probe inserted into fluid to be tested.

FIG. 1 illustrates part of a non-boil boiling point indicator device having a probe (2) and a display housing (31) shown schematically in FIG. 1 and similar to that shown in FIG. 2. The probe in FIG. 1 preferably projects from a bottom end of the display housing (31), and the power lead from the top or side thereof. The embodiment shown in FIG. 2 differs from the FIG. 1 device in that the display housing (31) is separate from the probe (2), the two parts being connected by a flexible lead (32).

The probe part of the boiling point indicator device (1) comprises an outer elongate tubular sheath or housing (3), preferably of stainless steel, in which is located a heater (4) for heating, for example, hygroscopic fluid such as motor vehicle brake fluid located within the housing, and a thermocouple (5) for use in measuring the temperature of fluid within the probe housing (3) during heating of the fluid.

A tubular sheath (6) lies co-axially within the tubular housing (3) for housing both the thermocouple (5) and electrical leads (7,8) connecting the heater (4) with electronic circuitry in the display housing (31) for controlling the operation of the heater. The electronic circuitry is in turn connected with a power source, which is not shown. The power source is preferably a battery of the motor vehicle for which the brake fluid is being tested. The electronic circuitry is not disclosed herewith in detail because it does not form part of the present invention.

The thermocouple (5), sheath (6), and leads (7,8) are held in position within the probe by a circular sealing disc (9) that extends transversely of the longitudinal axis of the tubular housing (3). The disc (9) seals off the end of the tubular housing containing the heater (4) from that part of the tubular housing which enters the display housing including the electronic circuitry referred to above. The thermocouple (5) and leads (7,8) pass through the disc (9) and are sealed relative thereto.

A shroud (20) is mounted on or forms a part of, the sheath (6) and diverges outwardly from the sheath to engage and lie coaxial with inner surface (21) of the tubular housing (3) of the probe (2). The form of the shroud serves to divide a portion (22) of the tubular housing (3) between disc (9) and an outer, or free, end (23) of the tubular housing (3) remote from the disc (9), into an outer and an inner chamber (24,25). The two chambers (24,25) are interconnected via non-restrictive apertures (26). The outer chamber (24) is in turn connected with the environment surrounding the probe housing (3) by non-restrictive apertures (27) around the tubular housing (3); only two apertures (27) of more than two apertures being indicated in FIG. 1. The inner chamber (25) is closed by a bung (28) in which there are a plurality of non-restrictive apertures (29) that connect the inner chamber (25) with the environment external to the probe. The non-restrictive apertures (29) allow free fluid flow into and out of the inner chamber.

In the embodiment of FIG. 1 the diverging shroud (20) is separate from the sheath (6) but is arranged to have a friction fit with a reduced diameter outer surface portion (6a) at the end of the sheath (6) that is adjacent the heater (4). The shroud (20) engages an end stop (6b) at the innermost end of the surface portion (6a). Alternatively, the sheath and shroud may be a single integral molding. As shown in FIG. 1, the portion (20a) of the shroud that engages the internal surface of the housing (3) is thicker than the portion that engages the portion (6a) of the sheath. This is to restrict the volume of the inner chamber (25) and so minimize the amount of fluid to be heated.

A shown in FIGS. 1 and 2, the display housing (31) houses a visual display (32). In cases where the indicator device (1) is being used to test the brake fluid of a motor vehicle and the power source is a battery of the vehicle, device (1) is operable once the vehicle is switched off and the power leads (33,34) of the test device are connected to the vehicle battery (36).

Immediately electrical power is applied to the indicator device (1) the display (32) will indicate the device is ready. The probe (2) is then dipped a number of times into hydraulic fluid (35) in the reservoir (37) provided for the hydraulic fluid of that vehicle so as to ensure the probe and fluid temperature are compatible. The probe is then dipped without stirring into the test fluid and held steady with the holes (27) in the side of the tubular housing (3) immersed in the hydraulic fluid.

To start the test, a start button is pressed and held. The start button is effective to operate the heater (4) for five seconds, or until the display (32) shows a moving pattern indicating the heater is on and the test is in progress. The moving display slows as the test nears completion. The brake fluid boiling point will then be displayed. The reading remains On-Screen on the display (32) until the device (1) is switched off or the start button is pressed for a further five seconds. operating the device (1) as described causes the probe heater (4) to be energized in a pulsatory manner. The first heating cycle is at high power and, at a set time within the cycle, the electronics look at the temperature reached by the heated fluid. This enables the fluid type to be determined and the power applied to the probe heater (4) during following cycles is reduced, according to the temperature reached, to prevent the heated fluid from reaching boiling point. The rising temperature of the fluid in subsequent heating cycles is monitored by control and calculating electronics in the electronic circuitry and, as the temperature rise slows, indicative of an approach to the boiling point but substantially before the boiling point is reached, the power to the probe heater is switched off. A boiling point indication is then derived using previously stored look-up tables within the electronics software and this temperature reading is displayed on the display (32) as the boiling point of the test fluid.

It is important when performing tests to perform at least two tests to avoid the effect of atmospheric moisture contamination on the probe. Having performed two tests the first reading can be disregarded.

Inaccurate readings will also occur if the heater (4) has not cooled sufficiently between tests and it is recommended that at least two minutes is allowed between the two tests. The cooling of the heater (4) can be achieved by repeatedly dipping the probe into cool, brake fluid. Methods of cooling involving stirring the fluid with the probe, or using compressed air, will provide distorted readings because of undue air bubbles appearing within the device and the fluid being stirred.

The electronic circuitry advantageously allows switching of temperature scales even when a final temperature reading is displayed.

Should the display (32) indicate an ERR2 reading the device (1) requires servicing. LO indicates a low battery, which will not allow the indicator device (1) to operate. Should the indicator device malfunction, the power connections should be checked first.

Figure 3A:
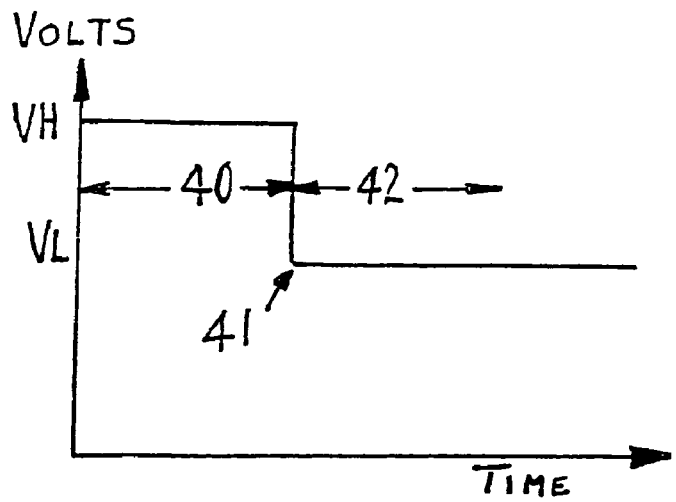
FIGS. 3a, 3b and 3c are graphs showing power input and fluid temperature rises against time.
Figure 3B:
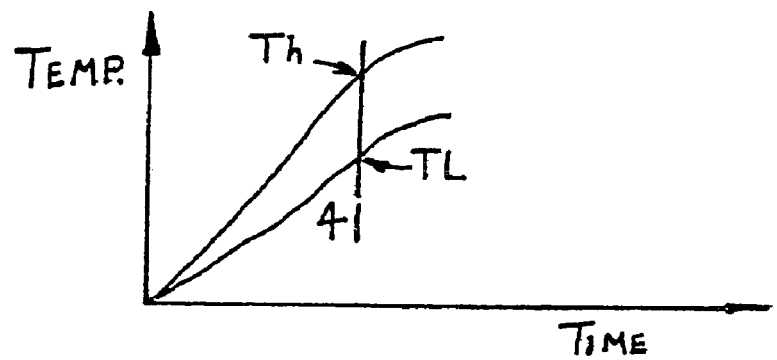

The graph of FIG. 3a illustrates an initial high power input (VH) over time (40) applied to the heater (4), which is then varied at and after a preset time (41) in accordance with the temperature attained by the semi-encapsulated test fluid at that time (41). The electronic control electronics decides at the preset test time (41) what the basic boiling point is of the type of fluid being tested. A low boiling point fluid is denoted by a low temperature rise, for example (TL) in FIG. 3b. The heater power input is lowered accordingly, for example, as shown at $V_L$. If the control and display electronics decide at the preset test time (41) that what is being tested is a high boiling point fluid, denoted by a high temperature rise for example (Th) in FIG. 3b, at the preset test time the heater power input (42) is accordingly increased to $V_H$ for example.

Figure 3C:
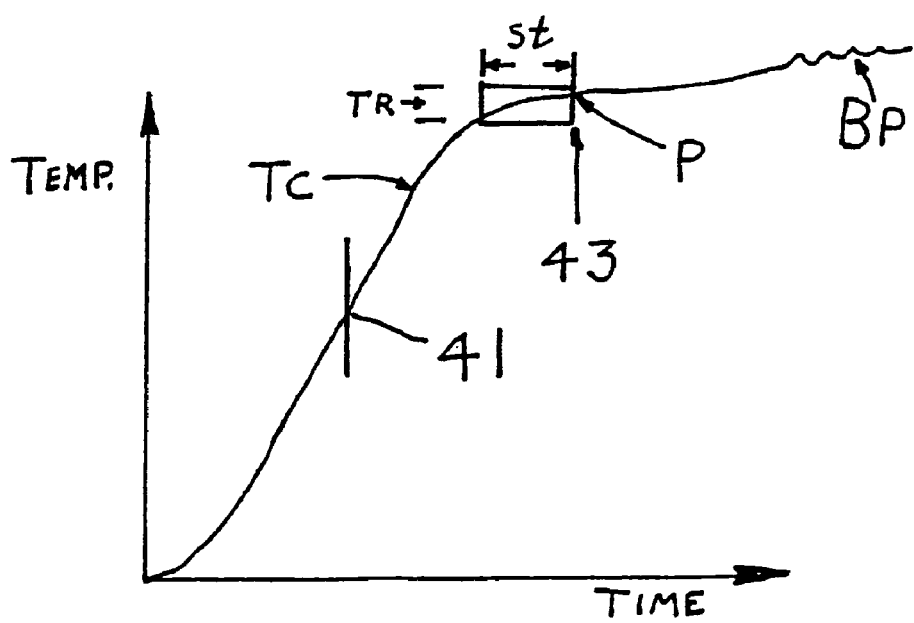

Referring to FIG. 3c, the rise in temperature curve (Tc) as sensed by the thermocouple (5) tends to flatten out at (P), a point ahead of the boiling point (BP). At this stage, the control and display electronics looks for a first point at which the temperature rise is less than a set amount (Tr) within a set time scale (St). A particular predetermined algorithm is used by the control and display electronics to equate the temperature in the calculation window (43) (using pre-programmed Calculus) to a figure equivalent to the actual boiling point (BP), or any other temperature reading required. That figure is shown on the display (32).

There has been described a boiling point indicator device having a restricted size fluid heating chamber situated at the free end (23) of the probe (2) with fluid inlet and outlet apertures (29) in a base (28) intermediate the inner chamber (25) and the fluid to be tested. Further apertures (27) are situated on the side of the probe housing at an appropriate set height to communicate with the outer chamber.

In use, at a predetermined time within the heating cycle, within the first few seconds, the electronics looks at the temperature reached by the heated fluid. A higher boiling point fluid will have attained a much higher temperature than a lower boiling point fluid. Using the temperature attained at and after the preset time as a guide, the power applied to the heating (4) is sustained, increased or reduced. This is done to prevent the heated fluid from being overheated or reaching boiling point. The rise in the temperature curve monitored by the temperature sensing device (thermocouple (5)) immersed in the heated fluid. The control and calculation electronics constantly looks for a set temperature rise within a set timescale, that can be used as a calculation window. As the temperature rise slows, substantially before the boiling point is reached, an extremely repeatable result can be extrapolated from a set temperature rise within a set time scale (the calculation window). Once this point is reached the power to the heater (4) is switched off. A temperature reading at a set time within the calculation window is correlated with stored "look up" tables held within the electronic software. This temperature reading within the calculation window (or any other repeatable temperature point) can be used to correlate the actual boiling point or any other temperature reading required. This boiling point temperature can be displayed as required on a suitable electronics display 32 such as that shown in FIGS. 1 and 2.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

I claim:

1. A non-boil boiling point indicator device, comprising:
   a) a probe;
   b) a control and electronic display connected with the probe;
   c) the probe including a housing having inner and outer chambers therein for receiving fluid to be tested;
   d) a plurality of non-restrictive apertures located between each of the inner and outer chambers and between the chambers and an external environment surrounding the housing and the non-restrictive apertures between the inner and outer chambers being located at the top of the inner chamber;
   e) a heater for heating fluid in the inner chamber; and
   f) a temperature sensing device configured and located in the inner chamber for sensing the temperature of a fluid being heated in the inner chamber; wherein the control and electronic display includes electronic circuitry that outputs a pulsed output to the heater for heating the fluid in a pulsed manner;
   g) wherein, in use, a change in rate of temperature rise is detected by the control and electronic display to equate to a preselected temperature reading, and wherein steam or vapor bubbles created adjacent the heater propel non-boiling test fluid above the heater relative to the direction of insertion of the probe in a fluid to be tested to overflow through the non-restrictive apertures between the inner and outer chambers.

2. A device as claimed in claim 1, wherein:
   a) the non-restrictive apertures are of a size and are configured for causing unrestricted vapor bubble flow therethrough.

3. A device as claimed in claim 1, wherein:
   a) the non-restrictive apertures between the inner and outer chambers are located at a top end of the chambers.

4. A device as claimed in claim 1, wherein:
   a) the unrestricted apertures located between the outer chamber and external environment are located at a bottom end of the outer chamber.

5. A device as claimed in claim 1, wherein:
   a) the inner chamber and housing are closed at a free end of the housing by a closure member having a plurality of non-restrictive apertures extending therethrough to allow free flow of fluid into and out of the inner chamber.

6. A device as claimed in claim 1, wherein:
   a) the heater comprises a heater element in the form of a wound coil.

7. A non-boil boiling point indicator device for determining the boiling point of fluids, the device comprising:
   a) a probe and a control and display device connected with the probe;
   b) the probe including:
      i) a housing having first and second chambers defined therein and being provided with respective non-restrictive apertures configured for providing free fluid communication between the first chamber and the second chamber and the second chamber and an exterior of the housing;
      ii) a heating device connected with electronic circuitry that provides a pulsed output to the heating device in order to heat a fluid to be tested in the first chamber in a pulsed manner; and
      iii) a temperature sensor for sensing the temperature of the fluid in the first chamber;
   c) the control and display device determining a boiling point temperature for the fluid in the first chamber using a sensed temperature which is lower than the boiling point temperature, and which sensed temperature is sensed at a time at which the control and display device determines a decrease in a rate of temperature rise in the fluid based on temperature sensed by the temperature sensor; and
   d) the heater heats the fluid in a pulsed manner and creates steam or vapor bubbles adjacent thereto which drive the fluid from the first chamber into the second chamber and to the exterior of the housing through the non-restrictive apertures.

8. A device as claimed in claim 7, wherein:
   a) the housing has a bottom end; and
   b) the non-restrictive apertures are provided in the bottom end and are configured for causing fluid to be tested to flow from a container of such fluid into the first chamber when the probe is inserted therein.

9. A device as claimed in claim 7, wherein:
   a) the housing has a bottom end; and
   b) the non-restrictive apertures providing fluid communication between the first and second chambers are disposed further from the bottom end than the non-restrictive apertures providing fluid communication between the second chamber and the exterior of the housing.

10. A non-boil boiling point indicator device, comprising:
    a) a probe;
    b) a control and electronic display connected with the probe;
    c) the probe including a housing having inner and outer chambers therein for receiving fluid to be tested;
    d) a plurality of non-restrictive apertures located between each of the inner and outer chambers at a top of the inner chamber, and between the chambers and an external environment surrounding the housing;
    e) a heater for heating fluid in the inner chamber;
    f) a temperature sensing device configured and located in the inner chamber for sensing the temperature of a fluid being heated in the inner chamber;
    g) the inner chamber being closed at a top end thereof and extending towards a free end of the housing, a first portion of a wall of the inner chamber defining a gap between it and the probe housing to define in part the outer chamber;

h) a second portion of the wall of the inner chamber engages the inner surface of the probe housing to close the outer chamber; and i) wherein, in use, a change in rate of temperature rise is detected by the control and electronic display to equate to a preselected temperature reading, and wherein steam or vapor bubbles created adjacent the heater propel non-boiling test fluid above the heater relative to the direction of insertion of the probe in a fluid to be tested to overflow through the non-restrictive apertures between the inner and outer chambers.

11. A device as claimed in claim 10, wherein:

a) the second portion of the wall of the inner chamber is thicker in a diametrical direction than the first portion to restrict the volume of the inner chamber and thereby minimize the amount of fluid heated by the heater.

12. A method of determining the boiling point of a fluid without boiling the fluid, the method comprising:

a) inserting a probe into a container of a fluid whose boiling point is to be determined, the probe having an inner chamber and an outer chamber and being provided with non-restrictive apertures communicating between the inner and outer chambers and between the outer chamber and the exterior environment, insertion of the probe into the fluid causing fluid to be received in the inner chamber;

b) heating the fluid in the inner chamber, bubbles created in the fluid by the heating thereof being able to freely propel fluid from the inner chamber to the outer chamber via the non-restrictive apertures communicating between the inner and outer chambers to overflow through the non-restrictive apertures communicating between the outer chamber and the exterior environment;

c) sensing the temperature of the fluid in the inner chamber;

d) monitoring the sensed temperature to detect a predetermined rate of temperature rise; and e) determining the boiling point temperature of the fluid using at least one temperature sensed when the predetermined temperature rise is detected, the at least one temperature being substantially below the boiling point temperature.

13. A non-boil boiling point indicator device, comprising:

a) a probe and a control and electronic display connected with the probe;

b) the probe including a housing extending from the control and electronic display and having inner and outer chambers therein for receiving fluid to be tested;

c) a plurality of non-restrictive apertures located between the inner and outer chambers and extending from the outer chamber through the probe housing;

d) a heater for heating fluid in the inner chamber, and a temperature sensing device located in part in the heater in the inner chamber for sensing the temperature of a fluid being heated in the inner chamber;

e) the inner and outer chambers being defined by a tubular sheath of reduced diameter relative to an internal diameter of the probe housing, and a shroud extending from the sheath to engage an internal surface of the probe housing to thereby to define the inner chamber within the shroud and the sheath, and the outer chamber between the shroud, sheath, and an internal surface of the probe housing, and close the outer chamber and restrict the volume of the inner chamber in the region of the heater;

f) a closure member extending across a free end of the probe housing remote from the control and electronics display, the closure member including at least one non-restrictive aperture extending therethrough; and g) wherein, in use, a change in the rate of temperature rise is detected by the control and electronic display to equate to a preselected temperature reading, and wherein steam or vapor bubbles created adjacent the heater can propel non-boiling test fluid above the heater relative to the direction of insertion of the probe in a fluid to be tested to overflow through the non-restrictive apertures between the inner and outer chambers, which are at the top of the inner chamber.

14. A non-boil boiling point indicator device for determining the boiling point of fluids, the device comprising:

a) a housing to be inserted in a fluid to be tested and a control and display device including electronic circuitry that provides a pulsed output;

b) the housing containing a first chamber and a second chamber, a heating device connected to the electronic circuitry, which provides a pulsed heating current in order to heat fluid to be tested in the first chamber in a pulsed manner and a temperature sensing device for sensing temperature of the fluid in the first chamber, a plurality of non-restrictive apertures being provided in the housing and configured and arranged such that, in use, steam or vapor bubbles generated by heating the fluid in a pulsed manner in the first chamber can propel non-boiling fluid from the first chamber out of the housing via the second chamber;

c) and the control and display device receiving signals from the temperature sensing device and being configured to determine a temperature indicative of a boiling temperature of the fluid in the first chamber from at least one sensed temperature lower than the boiling point temperature, the at least one sensed temperature being selected for the determination when signals from the temperature sensing device indicate a decrease in rate of temperature rise indicative of an approach to boiling point of the fluid in the first chamber but substantially before the boiling point is reached.

15. A device as claimed in claim 14, wherein:

a) a bottom end of the housing has a plurality of non-restrictive inlet apertures to the first chamber whereby a non-restrictive flowpath is provided through the housing between the inlet apertures and the non-restrictive apertures that cause fluid to be driven out of the housing, in use.

* * * * *